United States Patent [19]

Kazutoyo

[11] 4,326,877

[45] Apr. 27, 1982

[54] METHOD OF STIMULATING GRASS ROOT GROWTH WITH 6-BENZYLAMINOPURINE

[75] Inventor: Yahiro Kazutoyo, Chofu, Japan

[73] Assignee: Kabushiki Kaisha Kohjin, Tokyo, Japan

[21] Appl. No.: 154,876

[22] Filed: May 30, 1980

[30] Foreign Application Priority Data

Jun. 7, 1979 [JP] Japan .................................. 54-70602

[51] Int. Cl.$^3$ ............................................ A01N 43/50
[52] U.S. Cl. ............................................ 71/92; 71/77
[58] Field of Search ..................................... 71/77, 92

[56] References Cited

U.S. PATENT DOCUMENTS 2,966,488 12/1960 Shive et al. .............................. 71/77
3,070,432 12/1962 Strong et al. ........................... 71/92

OTHER PUBLICATIONS

Domanski et al., Chem. Abst. vol. 72 (1970) H2002w.
Galston et al., Control Mechanisms in Plant Development. (1970) Prentice Hall Inc.
Sargent et al., Chem. Abst. vol. 83 (1975) 109657j, (pp. 33092–Subject Index–included).
Babu et al., Chem. Abst. vol. 85 (1976) 42052d.

Primary Examiner—Catherine L. Mills
Attorney, Agent, or Firm—Stevens, Davis, Miller & Mosher

[57] ABSTRACT

A solution of 6-benzylaminopurine in a polar solvent dispersed in water and sprayed over the foliage of grass for the growth of grass roots in concentration of 25 to 300 p.p.m. The solution is sprayed onto the leaves and stems of grass at a rate at which 6-benzylaminopurine is applied in an amount of 2.5 to 30 mg. per m$^2$ of turf.

3 Claims, No Drawings

METHOD OF STIMULATING GRASS ROOT GROWTH WITH 6-BENZYLAMINOPURINE

BACKGROUND OF THE INVENTION

1. Field of the Invention:

The present invention relates to compositions and a method of use thereof for stimulating or increasing root growth of grasses and, more particularly, to compositions containing 6-benzylaminopurine as an active ingredient and a method of use thereof for a stimulant of grass root growth.

2. Brief Description of the Invention:

As agents of taking root for grasses there have heretofore been employed mainly fertilizers, trace element fertilizers, soil conditioning materials and the like. Agents for stimulating the growth of leaves and stems have also been employed for this purpose. These agents, however, fail to achieve sufficient effects.

An agent for stimulating or increasing the growth of grass roots or for making grasses take root by stimulating the root growth of grass is not yet known.

An application of fertilizers or agents for stimulating the growth of leaves and stems in a larger amount so as to stimulate the grass root growth may result in thickening the leaves and stems and have a tendency to decrease a resistance to disease, injury and circumstances such as drought, hot or cold weathers or the like.

$N^6$-Benzyladenine or 6-benzylaminopurine is a substance analogous in nature to kinetin. Kinetin is known to be effective in stimulating the sprouting of auxiliary buds and inducing the bud formation in the callus tissue culture.

It is also known in the publication of A. W. Galston & P. J. Davies; "Fundations of Developmental Biology Series: Control Mechanisms in Plant Development"(-Prentice-Hall, Inc. (1970); See: FIG. 5.6) that kinetin is ineffective in the growth of roots. And it is disclosed therein that kinetin, only when applied together with an auxin, such as indoleacetic acid, can stimulate the root growth.

Substances having properties in nature to kinetin are generally called cytokinin, and 6-benzyl-aminopurine has been said to be so similar in nature to kinetin that it belongs to cytokinin.

It is known that 6-benzylaminopurine was used for preventing the blasting in the forcing culture of tulips and was practically available for the growth of auxiliary buds of roses, the growth of buds of orchid cuttings, and for the blasting prevention of blossoms of vine plants.

It is disclosed in U.S. Pat. No. 3,070,432 that 6-benzylaminopurine, when used in combination with adenine, induced bud formation and, when used in admixture with an auxin such as indoleacetic acid, is effective for root growth.

It is nevertheless not known that 6-benzylaminopurine alone can stimulate or increase the growth of grass roots.

SUMMARY OF THE INVENTION

Accordingly, the object of the present invention is to provide compositions containing as an active ingredient 6-benzylaminopurine for use in the stimulation of the growth of grass roots.

Another object of the present invention is to provide a method of use of 6-benzylaminopurine for stimulating or increasing the growth of grass roots.

A further object of the present invention is the provision of a stimulant for the root growth producing favorable seedlings with well matted roots for sodding, said stimulant being effective for increasing matted roots in a small amount without excessive application of a fertilizer, and for growing grass roots in good balance with the leaves and stems, and improvements in the effects of turf on prevention of the dying of grasses, improved grass surface in appearance with roots satisfactorily matted, prevention of the turf destruction by well-matted roots, and the like.

DETAILED DESCRIPTION OF THE INVENTION

It now has been surprisingly found that 6-benzylaminopurine, which has been thought to be effective in growing the sprouting of auxiliary buds and inducing the bud formation in the callus tissue culture due to its similarity in nature to kinetin, is also effective in stimulating or increasing the growth of grass roots.

It has further been found that the effect of stimulating the grass root growth can be achieved even when a composition containing 6-benzylaminopurine as the sole ingredient is sprayed onto leaves of grasses. It is known that kinetin which has properties similar in nature to 6-benzylaminopurine is little transported within tissues of plants so that the effect of kinetin can be observed only on an area where kinetin is applied.

6-Benzylaminopurine which is an active ingredient of the compositions in accordance with the present invention, is a known compound and may be readily prepared, for example, by reacting adenine with benzylamine in conventional manner.

The compositions for spraying in accordance with the present invention may be prepared by diluting a solution (for example, an approximately 0.1% to 5% solution) of benzyladenine in a polar solvent such as dimethylformamide, propylene glycol or the like with water to a desired concentration. The spraying compositions may be mixed with other formulations such as adhesives which are non-toxic to grasses. The effective concentrations of 6-benzylaminopurine may range from approximately 25 p.p.m. to approximately 300 p.p.m. If the compositions are too dilute, the active ingredient is not retained on the applied leaf surfaces. If they are too concentrated, they are not uniformly sprayed and unnecessary amounts are sprayed. The spraying compositions may be sprayed in an amount of from approximately 2.5 to approximately 30 mg of 6-benzylaminopurine per $m^2$ of turf. Spraying amounts beyond this range do not achieve the desired effects.

The spraying may be conducted by spraying the compositions on grass surfaces, i.e., leaves and stems, of grasses. A time for spraying is not particularly limited in temperate regions and there is no difference in the effects from the difference of seasons.

The compositions according to the present invention may be sprayed immediately after planting of seedlings or sods or within a few weeks thereafter. They also may be sprayed together with fertilizer application or spraying of agricultural chemicals.

The compositions according to the present invention may be effective for grasses of the family Gramineae and grasses for turf and pasturage including grasses of the genus Zoisia, e.g. Japanese lawn grass (*Zoisia japonica*), Manila grass (*Zoisia matrella*) or mascarene grass (*Zoisia tenuifolia*), Bermuda grass (*Cynodon dactylon*), weeping lovegrass (*Eragrostis curvula*), bahiagrass (*Pas-* palum notatum), beach grasses, e.g. *Ammophila arenaria*, bentgrasses, e.g. colonial bent grass (*Agrostis tenuis*) or creeping bent grass (*Agrostis palustris*), blue grasses, e.g. Kentucky bluegrass (*Poa pratensis*), fescues, e.g. red fescue (*Festuca rubra*), ryegrasses, e.g. perennial ryegrass (*Lolium perenne*), orchard grass (*Dactylis glomerata*), or the like.

The compositions according to the present invention can accomplish the effect of stimulating and increasing the growth of grass roots and the effect which may be achieved by stimulation of and an increase in growth of grass roots is to provide active and strong seedlings and sods, increase in making root of seedlings, and ensure the development of turf. The compositions according to the present invention may permit the uniformity of the growth of grass leaves and stems and consequently provide turf favorable in appearance. The compositions according to the present invention increase resistance to drought and cold weather, prevent withering and yellowing, improve the growth on inappropriate soils, increase resistance to trampling of turf, permit an early recovery from injuries of grass leaves and stems and a favorable recovery after trimming, protection of pasturage and turf lands due to sliding, and strengthening the protection of ground faces and slopes such as banks, embankments, levees, developing lands, roads or the like, i.e. the prevention of soil erosion on account of wind, rain, flood or the like. These effects are achieved by an increase of matted roots in soil coverage by the growth of grass roots and an increase of recovering power by increased roots, which can also lead to economic benefits such as reduction in repairs upon development and saving maintenance and repairing costs.

The following examples will serve as illustrating the present invention more in detail, but should not be construed whatsoever as limiting the present invention thereto.

In the following examples, there were employed spraying solutions of 6-benzylaminopurine in concentrations of 25, 50, 100, and 200 p.p.m., which were prepared by diluting a 2% 6-benzylaminopurine in dimethyl formamide with water by 800-fold, 400-fold, 200-fold and 100-fold dilutions, respectively.

EXAMPLE 1

Twenty seedlings of Manila grass (*Zoisia matrella*) per pot, each weighting 1 gram, were planted on a 1/5,000-are Wagner pot. Immediately after planting, the spraying solutions in the concentrations indicated in Table below were sprayed thereonto by means of a pressurized atomizer at a rate of 100 ml per $m^2$. A fertilizer containing nitrogen, phosphorus and potassium ingredients was applied monthly at a rate of 30 grams per $m^2$.

This test was conducted at Ninomiya-cho, Tochigi-ken. The seedlings was planted on June 4, 1978 and the observation was conducted on September 1, 1978.

The results are shown in Table 1.

TABLE 1

| Plots | Weight of Leaves and Stems (Wet) | | Dry Weight of Stolon | | Dry Weight of Roots | | Length of Roots | |
|---|---|---|---|---|---|---|---|---|
| | g | % | g | % | g | % | g | % |
| Non-treatment | 14.8 | 100 | 9.62 | 100 | 5.18 | 100 | 15.5 | 100 |
| 50 p.p.m. | 16.05 | 108.4 | 10.43 | 108.4 | 5.61 | 108.3 | 15.8 | 101.9 |
| 100 p.p.m. | 20.65 | 139.5 | 13.82 | 143.6 | 7.72 | 149 | 23.5 | 151.6 |
| 200 p.p.m. | 21.63 | 146 | 14.05 | 146 | 7.75 | 149.6 | 24.8 | 160 |

EXAMPLE 2

Grass seedlings of Manila grass (Zoisia matrella) collected with a hole cutter were cut to root portions and top portions each of a predetermined length, washed with water and planted on an experimental field. The spraying solutions having the concentrations indicated in Table 2 below were sprayed onto each plot by means of a pressurized atomizer two weeks after the planting. A fertilizer containing nitrogen, phosphorous and potassium ingredients was applied monthly at a rate of 30 grams per $m^2$. The planting was conducted on May 21, 1978 at Ninomiya-cho, Tochigi-ken, and the observation was made on September 1.

TABLE 2

| Concentrations of Spraying Solutions | Percent Wet/Weight of Leaves | Dry Percent Weight of Stolon | Dry Percent Weight of Roots | Length of Roots | |
|---|---|---|---|---|---|
| | | | | (cm) | (%) |
| 0 | 100% | 100% | 100% | 11.0 | 100 |
| 50 p.p.m. | 101 | 101 | 106 | 13.6 | 123 |
| 100 p.p.m. | 194 | 168 | 184 | 25.5 | 231 |
| 200 p.p.m. | 171 | 151 | 164 | 23.3 | 211 |

It is recognized in Example 2 like in Example 1 that the spraying solutins according to the present invention stimulated the growth of roots and the weight of stolons and rooting.

EXAMPLE 3

Manila grass (*Zoisia matrella*) was cut with a cup having a 10 cm diameter and its leaves and roots were cut to a determined length to provide a 20-gram sample material which was then planted on a 1/50 $m^2$ Wagner pot. About two weeks later, spraying dispersions having the concentrations shown in Table 3 below were sprayed on the leaves and stems portions at a rate of 100 ml per $m^2$. A fertilizer containing nitrogen, phosphorus and potassium ingredients was monthly applied at a rate of 10 grams per $m^2$.

The seedlings were planted on Aug. 23, 1978 at Ushiku-cho, Ibaraki-ken, sprayed on September 4, and observed on November 15. The results are shown in Table 3.

TABLE 3

| Concentration of Solutions (p.p.m.) | Weight of Leaves & Stems | | Weight of Roots | |
|---|---|---|---|---|
| | g | (%) | g | (%) |
| 0 | 2.87 | (100) | 2.24 | (100) |
| 25 | 2.93 | (102) | 2.82 | (126) |
| 50 | 3.40 | (116) | 3.38 | (151) |
| 100 | 3.73 | (130) | 5.67 | (253) |
| 200 | 2.87 | (105) | 3.88 | (173) |

It is found from Table 3 that 6-benzylaminopurine, when applied in concentrations of from 25 to 200 p.p.m. (2.5 to 20 mg/$m^2$/plot), was effective and remarkably increased the root weight and it also increased the weight of leaves and stems. Accordingly, 6-benzylaminopurine achieved a remarkable effect for stimulating the growth of grass roots.

EXAMPLE 4

Seedlings of Manila grass (*Zoisia matrella*) were cut with a hole cutter to provide a turf piece (diameter, 10 cm; thickness, 2.5 cm) which was in turn planted on 1/5,000-are Wagner pot. A fertilizer (16 grams) comprising nitrogen, phosphorus and potassium (16:5:5) ingredients was applied per pot. Two weeks after the planting, the spraying solution in the concentrations indicated in Table 4 below were applied. This test was conducted in Fukuoka-shi, Fukuoka-ken.

TABLE 4

| Concentration of Solutions (p.p.m.) | Length of Leaves | | Weight of Leaves & Stems | | Weight of Roots | |
|---|---|---|---|---|---|---|
| | g | (%) | g | (%) | g | (%) |
| 0 | 35.3 | (100) | 24.0 | (100) | 9.5 | (100) |
| 50 | 36.6 | (104) | 26.5 | (110) | 15.0 | (158) |
| 100 | 35.7 | (101) | 24.0 | (100) | 11.0 | (116) |
| 200 | 35.5 | (101) | 27.5 | (115) | 11.0 | (116) |

The results as shown in Table 4 revealed that 6-benzylaminopurine is extremely effective for growing the grass roots.

EXAMPLE 5

The procedures of Example 3 was followed at the same experimental place with the exception that colonial bent grass was employed in place of Manila grass.

The grass was planted on February 24, sprayed with 6-benzylaminopurine on March 6, and observed on April 7. The results are shown in Table 5 below.

TABLE 5

| Concentration of Solutions (p.p.m.) | Weight of Leaves & Stems | | Weight of Roots | |
|---|---|---|---|---|
| | g | (%) | g | (%) |
| 0 | 2.10 | (100) | 1.54 | (100) |
| 25 | 2.20 | (105) | 1.77 | (115) |
| 50 | 2.54 | (121) | 2.62 | (170) |
| 100 | 2.65 | (126) | 4.36 | (283) |
| 200 | 2.18 | (104) | 2.23 | (145) |
| 300 | 2.17 | (103) | 1.85 | (120) |

It is found that plots where 6-benzylaminopurine in the concentrations of 25-300 ppm was applied permit an extremely stimulating growth of roots.

EXAMPLE 6

Seedlings of colonial bent grass (*Agrostis tenuis*) were cut a hole cutter and placed in super-saturated conditions for two weeks. The seedlings were cut to a determined length, and planted on 1/5000-are Wagner pot. A fertilizer (8 g) containing nitrogen, phosphorus and potassium ingredients was applied and the sprayed solutions were sprayed thereonto at a rate of 150 ml per $m^2$ in concentrations of 50 and 100 p.p.m., respectively.

The planting was carried out on March 6, 1979 at Katsudashi, Ibaraki-ken, and the spraying was made on Mar. 6, 1979. The grass was observed on Apr. 7, 1979.

The results revealed that the weights of roots were higher by 153% in the case of spraying of 50 p.p.m. and by 120% in the case of spraying 100 p.p.m. than no treatment was conducted. It is apparent that 6-benzylaminopurine was extremely effective for growing the grass roots. It is further found that colonial bent grasses in less nutritious conditions were brought into healthy conditions.

EXAMPLE 7

A 5×5 m. ground was sodded with colonial bent grass, and solutions in the concentrations of 50 and 100 p.p.m. respectively were sprayed at 100 ml per $m^2$ after one week (on June 15, 1978). On July 11, the turf was cut with a hole cutter. The sample turfs were observed to give a 195% increase in the length of grass roots where the solution in the concentration of 50 p.p.m. was sprayed and a 120% increase therein where the solution in the concentration of 100 p.p.m. was sprayed. This test was conducted in Nara-shi, Nara-ken.

EXAMPLE 8

A grass turf Penncross creeping bent grass was cut by a hole cutter, then cut to a determined length for the leaf and stem portions and the root portion, washed with water and then planted on a 1/5000-are sand pot. The seedlings were planted on May 21, 1978 at Ninomiya-shi, Tochigi-ken, sprayed with the solutions in the concentrations indicated in Table 6 below at a rate of 100 c.c. per $m^2$ on June 4. A fertilizer containing nitrogen, phosphorus and potassium ingredients was applied monthly in the amount of 30 g per $m^2$. The results are shown in Table 6 below.

In each of test plots, no injury from chemicals or inhibition of the growth of grass were recognized and the application of the solutions in the concentrations of 50 to 200 p.p.m. remarkably increased weights of roots and stolons.

TABLE 6

| Plots | Weight of Leaves and Stems (Wet) | | Dry Weight of Stolon | | Dry Weight of Roots | | Length of Roots | |
|---|---|---|---|---|---|---|---|---|
| | g | % | g | % | g | % | g | % |
| Non-treatment | 13.4 | 100 | 10.4 | 100 | 5.36 | 100 | 15.2 | 100 |
| 50 p.p.m. | 25.36 | 189 | 17.8 | 171 | 8.88 | 165 | 16.3 | 107 |
| 100 p.p.m. | 32.53 | 242 | 22.8 | 219 | 13.01 | 242 | 28.8 | 189.4 |
| 200 p.p.m. | 33.26 | 248 | 23.3 | 224 | 12.64 | 235 | 28.5 | 187.5 |

What is claimed is:

1. A method for stimulating the growth of grass roots, said method comprising spraying solution consisting essentially of diluted 6-benzylaminopurine on the leaves and stems of grass.

2. A method as claimed in claim 1, wherein the concentration of 6-benzylaminopurine in said solution is from about 25 p.p.m. to about 300 p.p.m.

3. A method as claimed in claim 1, wherein spraying deposits of from about 2.5 mg. to about 30 mg. of 6-benzylaminopurine per meter squared are utilized.

* * * * *